United States Patent [19]

Fuchs

[11] 4,127,600
[45] Nov. 28, 1978

[54] HERBICIDAL THIOLCARBAMATES

[75] Inventor: Julius J. Fuchs, Wilmington, Del.

[73] Assignee: E. I. Du Pont de Nemours and Company, Wilmington, Del.

[21] Appl. No.: 897,011

[22] Filed: Apr. 17, 1978

Related U.S. Application Data

[60] Division of Ser. No. 732,282, Oct. 13, 1976, which is a division of Ser. No. 520,114, Nov. 1, 1976, Pat. No. 4,004,915, which is a division of Ser. No. 356,422, May 2, 1973, Pat. No. 3,882,160, which is a continuation-in-part of Ser. No. 312,904, Dec. 7, 1972, Pat. No. 3,823,179.

[51] Int. Cl.$^2$ .......................................... C07C 153/09
[52] U.S. Cl. ............................................... 260/455 A
[58] Field of Search ................................... 260/455 A

[56] References Cited

U.S. PATENT DOCUMENTS 3,882,160  5/1975  Fuchs ................................ 260/455 A Primary Examiner—Lewis Gotts
Assistant Examiner—Robert C. Whittenbaugh

[57] ABSTRACT

Certain novel carbamates and thiolcarbamates are broad spectrum herbicides, which can be applied to the locus of undesired vegetation either preemergence or postemergence. Typical representatives of this class of compounds are methyl N-(N-cyclohexylcarbamoyl-N',N'-dimethylamidino)-N-methylcarbamate and methyl N-[1-(3-cyclohexyl-1-methylureido)-1-dimethylaminomethylene]carbamate.

1 Claim, No Drawings

HERBICIDAL THIOLCARBAMATES

CROSS-REFERENCE TO RELATED APPLICATION

This is a division of Ser. No. 732,282, filed Oct. 13, 1976, which is a division of Ser. No. 520,114, filed Nov. 1, 1974 and now U.S. Pat. No. 4,004,915, which is a division of Ser. No. 356,422, filed May 2, 1973 and now U.S. Pat. No. 3,882,160, which is a continuation-in-part of Ser. No. 312,904, filed Dec. 7, 1972 and now U.S. Pat. No. 3,823,179.

SUMMARY OF THE INVENTION

According to the present invention, it has now been discovered that certain novel carbamates and thiolcarbamates are effective and readily available herbicides. The compounds of this invention can be represented by the isomeric Formulas (1) and (2), which differ only in the position of the substituent $R_2$ with a concomitant shift of the double bond.

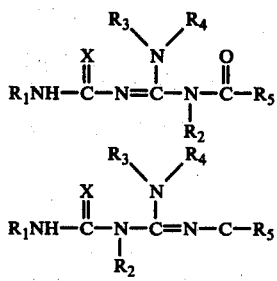

wherein
$R_1$ is selected from a $C_2$-$C_8$ alkyl substituted with 0–1 methoxy, ethoxy, methylthio, or ethylthio group; a $C_3$-$C_6$ alkenyl; a $C_3$-$C_6$ alkynyl; a $C_4$-$C_8$ cycloalkyl substituted with 0–1 $C_2$-$C_4$ alkyl, 0–2 methyl groups, 0–2 chlorine or bromine atoms, or 0–1 methoxy or ethoxy group; a $C_5$-$C_8$ cycloalkenyl; a $C_4$-$C_8$ cycloalkylmethyl or cycloalkenylmethyl; a $C_7$-$C_{10}$ bicycloalkyl or bicycloalkenyl; a $C_8$-$C_{11}$ bicycloalkylmethyl or bicycloalkenylmethyl; trimethylcyclohexyl; tetramethylcyclohexyl; and

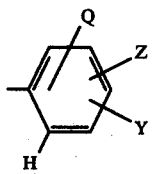

wherein
Q is hydrogen, fluorine, chlorine, bromine, a $C_1$-$C_4$ alkyl, a $C_1$-$C_2$ alkoxy or alkylthio group, nitro or trifluoromethyl group;
Y is hydrogen, chlorine, or methyl; and
Z is hydrogen or chlorine;
$R_2$ is a $C_1$-$C_3$ alkyl;
$R_3$ is hydrogen, methyl, or ethyl; $R_4$ is a $C_1$-$C_4$ alkyl, a $C_3$-$C_4$ alkenyl, a $C_3$-$C_4$ alkynyl, or methoxyl;
$R_5$ is —$OR_6$ or —$SR_6$, wherein $R_6$ is a $C_1$-$C_8$ alkyl substituted with 0–3 chlorine atoms or 0–1 methoxyl; and
X is oxygen or sulfur.

The compounds of this invention can be applied to the locus of weeds either preemergence or postemergence and provide excellent protection against a broad spectrum of weeds.

DETAILED DESCRIPTION OF THE INVENTION

Especially highly active and, therefore, preferred compounds of the present invention are those compounds represented by the above Formulas (1) and (2), wherein
$R_1$ is alkyl of 3 through 6 carbon atoms, cycloalkyl of 5 through 8 carbon atoms, or cycloalkyl of 5 through 8 carbon atoms substituted with one methyl group;
$R_2$, $R_3$ and $R_4$ are methyl; and
$R_5$ is $OR_6$.

Particularly preferred within this class are those compounds of Formulas (1) and (2) where
$R_1$ is cyclopentyl, methylcyclopentyl, cyclohexyl or methylcyclohexyl;
X is oxygen; and
$R_5$ is methoxyl.

The following reaction sequence I, which illustrates the preparation of methyl N-(N-cyclohexylcarbamoyl-N',N'-dimethylamidino)-N-methylcarbamate, is suitable for the preparation of most of the compounds of Formula (1) contemplated by this disclosure:

Sequence I
A)

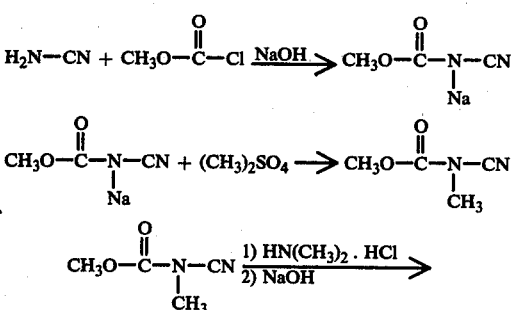

B)

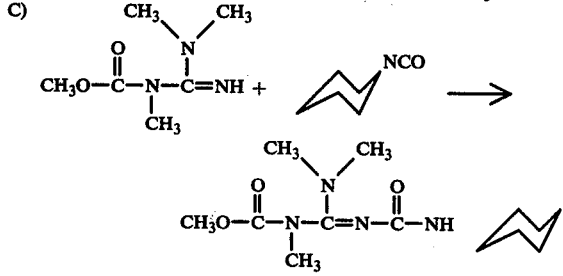

Other compounds of Formula (1) contemplated by this disclosure can be synthesized by a reaction of appropriate alkylcyanamides with

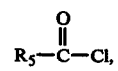

where $R_5$ has the above-defined meaning. This reaction is shown below as the first step of Sequence II.

Sequence II

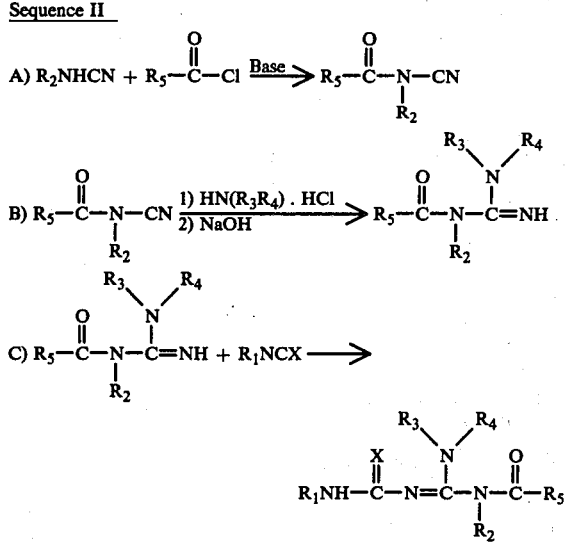

The following reaction sequence III, which illustrates the preparation of methyl N-[1-(3-cyclohexyl-1-methylureido)-1-dimethylaminomethylene]carbamate is suitable for the preparation of the compounds of the isomeric Formula (2).

Sequence III

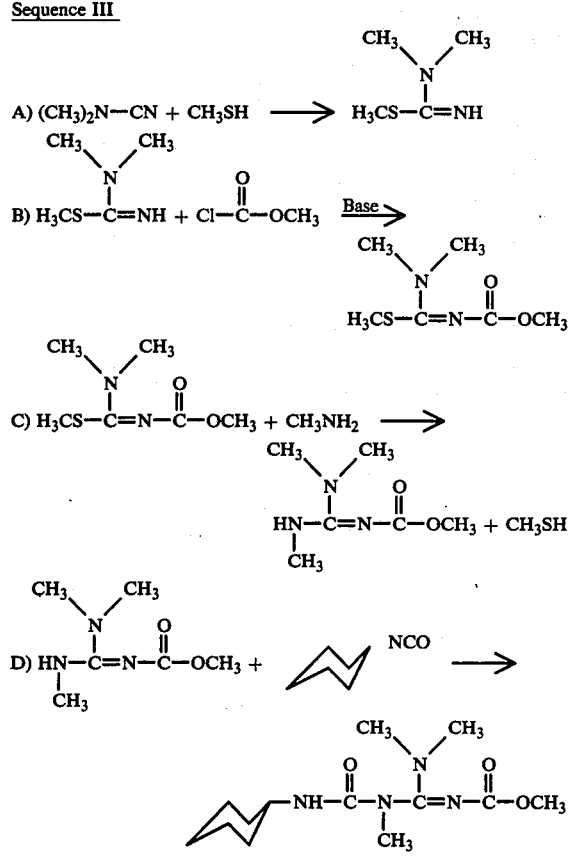

These preparations are described in the following Examples, wherein all the proportions, parts, and percentages are by weight.

EXAMPLE 1

(A) Synthesis of N-Methoxycarbonyl-N-Methylcyanamide

To a solution of 504 parts of a 50% aqueous cyanamide solution in 825 parts of water at 25° C. are added during a period of 90 minutes and at a pH of 6.9-7.1 simultaneously 572 parts of methyl chloroformate and 945 parts of a 50% aqueous sodium hydroxide solution. As the addition of the reactants progresses, the temperature of the reaction is allowed to rise to 53°-55° C. and is maintained within that range by cooling. When the addition is complete, the reaction mass is cooled to 25° C., whereupon crystallization of the sodium salt of methoxycarbonylcyanamide occurs. Dimethyl sulfate (775 parts) is then added, and agitation of the reaction mass is continued while maintaining the pH at 7-7.1 by a dropwise addition of about 25 parts of a 50% aqueous sodium hydroxide solution. After 6.5 hours, the resulting two-phase solution is repeatedly extracted with methylene chloride and the extract is dried. One half of the methylene chloride extract is then evaporated under vacuum, and the residue is distilled at 50° C./0.5 mm. There is obtained 237.6 parts of N-methoxycarbonyl-N-methylcyanamide (69.5% yield).

(B) Synthesis of N-Methoxycarbonyl-N',N'-Trimethylguanidine

A solution of 339 parts of dimethylamine hydrochloride in 500 parts of water is heated to 50° C., and the remaining one half of the above methylene chloride extract is added to it gradually, while at the same time removing the methylene chloride by distillation. The resulting two-phase mixture is then heated for approximately 20 hours at 80° C., after which time the starting N-methoxycarbonyl-N-methylcyanamide has nearly completely disappeared. The solution is then cooled to 0° C., and 336 parts of a 50% aqueous sodium hydroxide is added. Repeated extraction of the reaction solution with methylene chloride and evaporation of the methylene chloride under vacuum gives 228.6 parts of crude N-methoxycarbonyl-N,N',N'-trimethylguanidine of 84.4% purity, from which the pure product is isolated by distillation at 72° C./0.5 mm.

(C) Synthesis of Methyl N-(N-cyclohexylcarbamoyl-N',N'-dimethylamidino)-N-methylcarbamate To 14.8 parts of the above crude N-methoxycarbonyl-N,N',N'-trimethylguanidine in 50 parts of methylene chloride is added 11.0 parts of cyclohexyl isocyanate. The solution temperature reaches the boiling point, and when the temperature has fallen to 25° C., the solvent is evaporated under vacuum to give an oil, which crystallizes when triturated with ether. Recrystallization from a mixture of carbon tetrachloride and petroleum ether gives pure methyl N-(N-cyclohexylcarbamoyl-N',N'-dimethylamidino)-N-methylcarbamate, m.p. 93°-94° C.

Using appropriate starting materials, the following compounds can be prepared in a similar manner.

TABLE I methyl N-(N-n-hexylcarbamoyl-N',N'-dimethylamidino)-N-methylcarbamate
methyl N-(N-isopropylcarbamoyl-N',N'-dimethylamidino)-N-methylcarbamate
methyl N-[N-(4-methoxycyclohexylcarbamoyl-N'N'-dimethylamidino)]-N-methylcarbamate

TABLE I-continued

| Compound | |
|---|---|
| methyl N-[N-(3,4-dimethylcyclohexylcarbamoyl-N',N'-dimethylamidino)]-N-methylcarbamate | |
| methyl N-[N-(4-chlorophenylcarbamoyl)-N',N'-dimethylamidino]-N-methylcarbamate | |
| methyl N-[N-(2-chlorophenylcarbamoyl)-N',N'-dimethylamidino]-N-methylcarbamate | |
| methyl N-[N-(3-methylphenylcarbamoyl)-N',N'-dimethylamidino]-N-methylcarbamate | m.p. 145° C |
| methyl N-[N-(4-methylphenylcarbamoyl)-N',N'-dimethylamidino]-N-methylcarbamate | m.p. 127° C |
| methyl N-(N-cyclopentylcarbamoyl-N',N'-dimethylamidino)-N-methylcarbamate | |
| methyl N-(N-cyclooctylcarbamoyl-N,N'-dimethylamidino)-N-methylcarbamate | |
| methyl N-[N-(3-fluorophenylcarbamoyl)-N',N'-dimethylamidino]-N-methylcarbamate | m.p. 126° C |
| methyl N-[N-(4-fluorophenylcarbamoyl)-N',N'-dimethylamidino]-N-methylcarbamate | m.p. 95–97.5° C |
| methyl N-(N-n-butylcarbamoyl-N',N',-dimethylamidino)-N-methylcarbamate | |
| methyl N-(N-n-propylcarbamoyl-N',N'-dimethylamidino)-N-methylcarbamate | |
| methyl N-[N-(4-bromophenylcarbamoyl-N',N'-dimethylamidino)]-N-methylcarbamate | m.p. 242–247° C |
| methyl N-[N-(1-decahydronaphthylcarbamoyl)-N',N'-dimethylamidino]-N-methylcarbamate | |
| methyl N-[N-(4-flourophenylthiocarbamoyl)-N'N'-dimethylamidino]-N-methylcarbamate | m.p. 132–133° C |
| methyl N-(N-cyclohexylthiocarbamoyl-N',N'-dimethylamidino)-N-methylcarbamate | m.p. 122–123° C |
| methyl N-(N-phenylthiocarbamoyl-N',N'-dimethylamidino)-N-methylcarbamate | m.p. 155–157° C |
| methyl N-[N-(3-fluorophenylthiocarbamoyl)-N',N'-dimethylamidino]-N-methylcarbamate | m.p. 121–122° C |
| methyl N-[N-(3,4-dichlorophenylcarbamoyl)-N',N'-dimethylamidino]-N-methylcarbamate | m.p. 146° C |
| methyl N-[N-(4-methoxyphenylcarbamoyl)-N',N'-dimethylamidino]-N-methylcarbamate | |
| methyl N-(N-allylcarbamoyl-N',N'-dimethylamidino)-N-methylcarbamate | |
| methyl N-[N-(2-fluorophenylcarbamoyl)-N',N'-dimethylamidino]-N-methylcarbamate | |
| methyl N-(N-cyclohexylmethylcarbamoyl-N',N'-dimethylamidino)-N-methylcarbamate | |
| methyl N-(N-ethylcarbamoyl-N',N'-dimethylamidino)-N-methylcarbamate | |
| methyl N-[N-(2-hexen-1-ylcarbamoyl)-N',N'-dimethylamidino]-N-methylcarbamate | |
| methyl N-(N-propargylcarbamoyl-N',N'-dimethylamidino)-N-methylcarbamate | |
| methyl N-[N-(2-hexyn-1-ylcarbamoyl)-N',N'-dimethylamidino]-N-methylcarbamate | |
| methyl N-[N-(1,3-dimethylbutylcarbamoyl)-N',N'-dimethylamidino]-N-methylcarbamate | |
| methyl N-[N-(1-ethylpropylcarbamoyl)-N',N'-dimethylamidino]-N-methylcarbamate | |
| methyl N-[N-(1-isopropyl-2-methylpropylcarbamoyl)-N',N'-dimethylamidino]-N-methylcarbamate | |
| methyl N-[N-(1,2,2-trimethylpropylcarbamoyl)-N',N'-dimethylamidino]-N-methylcarbamate | |
| methyl N-(N-n-pentylcarbamoyl-N,N'-dimethylamidino)-N-methylcarbamate | |
| methyl N-[N-(1-methylbutylcarbamoyl)-N',N'-dimethylamidino]-N-methylcarbamate | |
| methyl N-[N-(3-trifluoromethylphenylcarbamoyl)-N',N'-dimethylamidino]-N-methylcarbamate | |
| methyl N-(N-n-octylcarbamoyl-N',N'-dimethylamidino)-N-methylcarbamate | |
| methyl N-[N-(2-methylcyclohexylcarbamoyl)-N',N'-dimethylamidino]-N-methylcarbamate | |
| methyl N-[N-(3-methylcyclohexylcarbamoyl)-N',N'-dimethylamidino]-N-methylcarbamate | |
| methyl N-(N-cycloheptylcarbamoyl-N',N'-dimethylamidino)-N-methylcarbamate | |
| methyl N-(N-cyclohexylmethylcarbamoyl-N',N'-dimethylamidino)-N-methylcarbamate | |
| methyl N-[N-(2-cyclohexenylcarbamoyl)-N',N'-dimethylamidino]-N-methylcarbamate | |
| methyl N-[N-(3-cyclohexenylcarbamoyl)-N',N'-dimethylamidino]-N-methylcarbamate | |
| methyl N-(N-cyclohexenylmethylcarbamoyl-N',N'-dimethylamidino)-N-methylcarbamate | |
| methyl N-[N-(2-cyclooctenylcarbamoyl)-N',N'-dimethylamidino]-N-methylcarbamate | |
| methyl N-(N-norbornylcarbamoyl-N',N'-dimethylamidino)-N-methylcarbamate | |
| methyl N-(N-norbornylmethylcarbamoyl-N',N'-dimethylamidino)-N-methylcarbamate | |
| methyl N-(N-norbornenylcarbamoyl-N',N'-dimethylamidino)-N-methylcarbamate | |
| methyl N-(N-norbornenylmethylcarbamoyl-N',N'-dimethylamidino)-N-methylcarbamate | |
| methyl N-[N-(2,3,5-trimethylcyclohexylcarbamoyl)-N',N'-dimethylamidino]-N-methylcarbamate | |
| methyl N-[N-(2,3,5,6-tetramethylcyclohexylcarbamoyl)-N',N'-dimethylamidino]-N-methylcarbamate | |
| methyl N-[N-(3,3,5,5-tetramethylcyclohexylcarbamoyl)-N',N'-dimethylamidino]-N-methylcarbamate | |
| methyl N-[N-(2-chlorocyclohexylcarbamoyl)-N',N'-dimethylamidino]-N-methylcarbamate | |
| methyl N-[N-(1-methylcyclopentylcarbamoyl)-N',N'-dimethylamidino]-N-methylcarbamate | |
| methyl N-[N-(2,3-dichlorocyclohexylcarbamoyl)-N',N'-dimethylamidino]-N-methylcarbamate | |
| methyl N-[N-(p-methoxycyclohexylcarbamoyl)-N',N'-dimethylamidino]-N-methylcarbamate | |
| methyl N-[N-(4-ethoxycyclohexylcarbamoyl)-N',N'-dimethylamidino]-N-methylcarbamate | |
| methyl N-[N-(2-ethylcyclohexylcarbamoyl)-N',N'-dimethylamidino]-N-methylcarbamate | |
| methyl N-[N-(4-tert-butylcyclohexylcarbamoyl)-N',N'-dimethylamidino]-N-methylcarbamate | |
| methyl N-(N-cyclohexylthiocarbamoyl-N',N'-dimethylamidino)-N-methylcarbamate | |
| methyl N-(N-cyclopentylthiocarbamoyl-N',N'-dimethylamidino)-N-methylcarbamate | |
| methyl N-[N-(2-methylcyclohexylthiocarbamoyl)-N',N'-dimethylamidino]-N-methylcarbamate | |
| methyl N-(N-cyclooctylcarbamoyl-N'-butylamidino)-N-methylcarbamate | |
| methyl N-(N-cyclopentylcarbamoyl-N'-allylamidino)-N-methylcarbamate | |
| methyl N-(N-neopentylcarbamoyl-N',N'-dimethylamidino)-N-methylcarbamate | |
| ethyl N-(N-cyclohexylcarbamoyl-N',N'-dimethylamidino)-N-methylcarbamate | |
| ethyl N-(N-propargylcarbamoyl-N',N'-dimethylamidino)-N-methylcarbamate | |
| ethyl N-(N-hexyn-2-ylcarbamoyl-N',N'-dimethylamidino)-N-methylcarbamate | |
| ethyl N-[N-allylcarbamoyl-N'-(2-methylallyl)amidino]-N-methylcarbamate | |
| ethyl N-(N-buten-2-ylcarbamoyl-N',N'-dimethylamidino)-N-methylcarbamate | |
| ethyl N-[N-(2-cyclopentenylcarbamoyl)-N',N'-dimethylamidino]-N-methylcarbamate | |
| butyl N-(N-cyclohexylcarbamoyl-N',N'-dimethylamidino)-N-methylcarbamate | |
| octyl N-(N-cyclohexylcarbamoyl-N',N'-dimethylamidino)-N-methylcarbamate | |
| octyl N-[N-(2,6-dimethylcyclohexylcarbamoyl)-N',N'-dimethylamidino]-N-methylcarbamate | |
| octyl N-[N-(2-norbornylcarbamoyl)-N',N'-dimethylamidino]-N-methylcarbamate | |
| methyl N-[N-(2-methylthiopropylcarbamoyl)-N',N'-dimethylamidino]-N-ethylcarbamate | |
| methyl N-[N-(1-methylcyclohexylcarbamoyl)-N',N'-dimethylamidino]-N-ethylcarbamate | |
| methyl N-(N-cyclohexylcarbamoyl-N',N'-dimethylamidino)-N-ethylcarbamate | |
| methyl N-[N-(p-methylthiophenylcarbamoyl)-N'-methylamidino]-N-methylcarbamate | |
| methyl N-(N-cyclohexylcarbamoyl-N'-methylamidino)-N-methylcarbamate | |
| methyl N-[N-(3-chloro-4-butylphenylcarbamoyl)-N'-propargylamidino]-N-methylcarbamate | |
| methyl N-[N-(4-ethoxyphenylcarbamoyl)-N'-butyn-2-ylamidino]-N-methylcarbamate | |
| 2,2,2-trichloroethyl N-[N-(p-ethylthiophenylcarbamoyl)-N',N'-dimethylamidino]-N-methylcarbamate | |
| 2-methoxyethyl N-(N-cyclobutylcarbamoyl-N',N'-dimethylamidino)-N-methylcarbamate | |
| methyl N-(N-cyclopropylmethylcarbamoyl-N',N'-dimethylamidino)-N-methylcarbamate | |
| methyl N-(N-cycloheptylmethylcarbamoyl-N',N'-diethylamidino)-N-methylcarbamate | |
| methyl N-(N-cyclopropen-2-ylmethylcarbamoyl-N',N'-dimethylamidino)-N-methylcarbamate | |
| methyl N-[N-(cyclohepten-4-ylmethylcarbamoyl)-N',N'-dimethylamidino]-N-methylcarbamate | |
| methyl N-[N-(1-decahydronaphthylmethylcarbamoyl)-N',N'-dimethylamidino]-N-methylcarbamate | |
| methyl N-[N-(1-decahydronaphthen-2-ylmethylcarbamoyl)-N',N'-dimethylamidino]-N-methylcarbamate | |
| methyl N-(N-cyclohexylcarbamoyl-N'-butylamidino)-N-methylcarbamate | |
| methyl N-[N-(3-chloro-4-methylthiophenylcarbamoyl)-N'-(2-methylallyl)amidino]-N-methylcarbamate | |
| methyl N-(N-cyclohexylcarbamoyl-N'-methoxy-N'-methylamidino)-N-methyl carbamate | |
| methyl N-(N-cyclohexylcarbamoyl-N'-butyl-N'-methylamidino)-N-methylcarbamate | |
| methyl N-[N-(2-decahydronaphthylcarbamoyl)-N',N'-dimethylamidino]-N-methylcarbamate | |
| methyl N-[N-(2-norbornylcarbamoyl)-N',N'-dimethylamidino]-N-methylcarbamate | |
| methyl N-[N-(2-norbornylcarbamoyl)-N'-methylamidino]-N-methylcarbamate | |

TABLE I-continued methyl N-[N-(p-tolylcarbamoyl)-N',N'-dimethylamidino]-N-methylcarbamate
methyl N-(N-cyclohexylcarbamoyl-N',N'-dimethylamidino)-N-methylthiolcarbamate
methyl N-(N-cyclopentylcarbamoyl-N',N'-dimethylamidino)-N-methylthiolcarbamate
methyl N-[N-(2-methylcyclohexyl)-N',N'-dimethylamidino]-N-methylthiolcarbamate
methyl N-[N-(3-methylcyclohexyl)-N',N'-dimethylamidino]-N-methylthiolcarbamate
methyl N-(N-cycloheptylcarbamoyl-N',N'-dimethylamidino)-N-methylthiolcarbamate
methyl N-(N-cyclooctylcarbamoyl-N',N'-dimethylamidino)-N-methylthiolcarbamate
methyl N-(N-cyclohexylmethylcarbamoyl-N',N'-dimethylamidino)-N-methylthiolcarbamate
methyl N-(N-norbornylcarbamoyl-N,N'-dimethylamidino)-N-methylthiolcarbamate
methyl N-(N-cyclohexen-2-ylcarbamoyl-N',N'-dimethylamidino)-N-methylthiolcarbamate
methyl N-(N-phenylcarbamoyl-N',N'-dimethylamidino)-N-methylthiolcarbamate
methyl N-[N-(3,4-dichlorophenylcarbamoyl)-N',N'-dimethylamidino]-N-thiolcarbamate

EXAMPLE 2

(A) Synthesis of 1,1-Dimethyl-2-methyl-2-thio-pseudourea

Methyl mercaptan (27 parts) and concentrated sulfuric acid are added with good agitation to a solution of 35 parts of dimethylcyanamide in 150 parts of water. The methyl mercaptan addition requires 40 minutes. The sulfuric acid is added on demand to maintain a pH of 9.5 ± 0.2. The acid addition is stopped when the pH remains constant at 9.5 without further adjustment. This requires an additional 35 minutes.

The temperature is maintained at 25° ± 2° C. by external cooling. Loss of mercaptan from the system is prevented by the use of a dry ice/acetone condenser.

When the above reaction is complete, the pH is adjusted to 5.3 and 20 mls of distillate is removed at 18 mm Hg by heating the pot to 33° C.

(B) Synthesis of Methyl N-(1-Dimethylamino-1-methylthiomethylene)carbamate

Methylene chloride (174 parts) is now added to the above pot residue and 48.9 parts of methyl chloroformate is added during 112 minutes at 5° ± 5° C. while 50% aqueous caustic is simultaneously added on demand with good agitation at a rate such that the pH is maintained at 9.5 ± 0.2. The caustic addition is continued at 10° C. until the pH remains constant. This requires about four more hours.

The lower methylene chloride layer is removed, the pH adjusted to 11.0 with 50% caustic, and the aqueous phase extracted twice with 150 mls of methylene chloride. The combined extracts are evaporated to constant weight on a rotary evaporator to give 78.5 parts of crude methyl N-(1-dimethylamino-1-methylthiomethylene)carbamate as an oil which is purified by vacuum fractionation to give 59.8 parts of product, b.p. 103° C. at 0.4 mm Hg.

(C) Synthesis of Methyl N-(1-Dimethylamino-1-methylaminomethylene)carbamate

The above distillate is added to a solution of 28.6 parts of monomethylamine in 423 parts of toluene and stirred in a closed system for 24 hours. The reaction mass is then evaporated to constant weight on a rotary evaporator to give 55 parts of an oil which solidifies on standing overnight, m.p. 80°-85° C. Recrystallization from toluene-heptane gives 41.0 parts of methyl N-(1-dimethylamino-1-methylaminomethylene) carbamate as a pure white crystalline material, m.p. 87°-89° C.

(D) Synthesis of Methyl N-[1-(3-Cyclohexyl-1-methylureido)-1-dimethylaminomethylene]carbamate The above product is dissolved in a solution of 32.2 parts of cyclohexyl isocyanate in 510 parts of 1,2-dichloroethane and heated under reflux for 2 hours. The reaction mass is cooled to room temperature, and 586 parts of water is added. The pH of the resulting aqueous phase is adjusted to approximately 2 with conc. hydrochloric acid. The aqueous phase is separated, 1020 parts of 1,2-dichloroethane added to it, and enough 50% caustic is added to adjust the pH of the aqueous phase to 10 to 11. The mixture is shaken and the 1,2-dichloroethane layer evaporated to constant weight on a rotary evaporator to give 43.0 gms of oil, which crystallizes on standing to give an impure solid, m.p. 60-75. Recrystallization from toluene-heptane gives 16.3 parts of methyl N-[1-(3-cyclohexyl-1-methylureido)-1-dimethylaminomethylene]carbamate as pure white crystals, m.p. 81°-82° C.

Using the appropriate starting materials, the following compounds can be prepared in a similar manner.

methyl N-[1-(3-n-pentyl-1-methylureido)-1-dimethylaminomethylene]carbamate
methyl N-[1-(3-cyclohexylmethyl-1-methylureido)-1-dimethylaminomethylene]carbamate
methyl N-[1-(3-n-propyl-1-methylureido)-1-dimethylaminomethylene]carbamate
methyl N-[1-(3-n-butyl-1-methylureido)-1-dimethylaminomethylene]carbamate
methyl N-[1-(3-n-hexyl-1-methylureido)-1-dimethylaminomethylene]carbamate
methyl N-[1-(3-n-octyl-1-methylureido)-1-dimethylaminomethylene]carbamate
methyl N-{1-[3-(1,3-dimethylbutyl)-1-methylureido]-1-dimethylaminomethylene}carbamate
methyl N-{1-[3-(1-ethylpropyl)-1-methylureido]-1-dimethylaminomethylene}carbamate
methyl N-{1-[3-(1-isopropyl-2-methylpropyl)-1-methylureido]-1-dimethylaminomethylene}carbamate
methyl N-{1-[3-(1,2,2-trimethylpropyl)-1-methylureido]-1-dimethylaminomethylene}carbamate
methyl N-[1-(3-neopentyl-1-methylureido)-1-dimethylaminomethylene]carbamate
methyl N-{1-[3-(1-methylbutyl)-1-methylureido]-1-dimethylaminomethylene}carbamate
methyl N-{1-[3-(3-trifluoromethylphenyl)-1-methylureido]-1-dimethylaminomethylene}carbamate
methyl N-[1-(3-ethyl-1-isopropylureido)-1-diethylaminomethylene]carbamate
methyl N-[1-(3-butyl-1-propylureido)-1-methyl-1-propylaminomethylene]carbamate
methyl N-[1-(3-octyl-1-methylureido)-1-allylaminomethylene]carbamate
methyl N-{1-[3-(2-norbornyl)-1-methylureido]-1-dimethylaminomethylene}carbamate
methyl N-[1-(3-phenyl-1-methylureido)-1-dimethylaminomethylene]carbamate methyl N-{1-[3-(p-chlorophenyl)-1-methylureido]-1-dimethylaminomethylene}carbamate methyl N-{1-[3-(3,4-dichlorophenyl)-1-methylureido]-1-dimethylaminomethylene]carbamate ethyl N-[1(3-cyclohexyl-1-methylureido)-1-dimethylaminomethylene]carbamate ethyl N-[1-(3-cyclooctyl-1-methylureido)-1-dimethylaminomethylene]carbamate ethyl N-[1-(3-phenyl-1-methylureido)-1-dimethylaminomethylene]carbamate ethyl N-{1-[3-(m-tolyl)-1-methylureido]-1-dimethylaminomethylene}carbamate octyl N-[1-(3-cyclohexyl-1-methylureido)-1-dimethylaminomethylene]carbamate methyl N-{1-[3-(2-ethoxybutyl)-1-methylureido]-1-dimethylaminomethylene}carbamate methyl N-{1-[3-(2-methylthiobutyl)-1-methylureido]-1-dimethylaminomethylene}carbamate ethyl N-{1-[3-(2-ethylthiopropyl)-1-methylureido]-1-dimethylaminomethylene}carbamate hexyl N-[1-(3-cyclohexyl-1-methylureido)-1-dimethylaminomethylene]carbamate hexyl N-[1-(3-cyclopentyl-1-methylureido)-1-dimethylaminomethylene]carbamate hexyl N-[1-(3-phenyl-1-methylureido)-1-dimethylaminomethylene]carbamate isopropyl N-[1-(3-cyclohexyl-1-methylureido)-1-dimethylaminomethylene]carbamate isopropyl N-[1-(3-norbornyl-1-methylureido)-1-dimethylaminomethylene]carbamate isopropyl N-{1-[3-(o-fluorophenyl)-1-methylureido]-1-dimethylaminomethylene}carbamate isopropyl N-{1-[3-(2-propenyl)-1-methylureido]1-dimethylaminomethylene}carbamate methyl N-{1-[3-(3-methoxypropyl)-1-methylureido]1-dimethylaminomethylene}carbamate methyl N-{1-[3-(2-chlorocyclohexyl)-1-methylureido]-1-dimethylaminomethylene}carbamate methyl N-{1-[3-(2,3-dichlorocyclohexyl)-1-methylureido]1-dimethylaminomethylene}carbamate methyl N-{1-[3-(2-bromocyclohexyl)-1-methylureido]-1-dimethylaminomethylene}carbamate methyl N-{1-[3-(2-methylcyclohexyl)-1-methylureido]-1-dimethylaminomethylene}carbamate methyl N-{1-[3-(2,6-dimethylcyclohexyl)-1-methylureido]1-dimethylaminomethylene}carbamate methyl N-{1-[3-(2-butylcyclopentyl)-1-methylureido]-1-dimethylaminomethylene}carbamate methyl N-{1-[3-(2-norbornyl)-1-methylureido]-1-diethylaminomethylene}carbamate methyl N-{1-[3-(cyclohexen-2-yl)-1-methylureido]-1-dimethylaminomethylene]carbamate methyl N-{1-[3-(cyclopenten-2-yl)-1-methylureido]-1-dimethylaminomethylene}carbamate ethyl N-[1-(3-norbornyl-1-methylureido)-1-dimethylaminomethylene]carbamate isopropyl N-[1-(3-norbornyl-1-methylureido)-1-dimethylaminomethylene]carbamate methyl N-{1-[3-(4-isopropylcyclohexyl)-1-methylureido]1-dimethylaminomethylene}carbamate ethyl N-{1-[3-(p-tolyl)-1-methylureido]-1dimethylaminomethylene}carbamate ethyl N-{1-[3-(m-nitrophenyl)-1-methylureido]-1-dimethylaminomethylene}carbamate ethyl N-{1-[3-(3-chloro-4-isopropylphenyl)-1-methylureido]1-dimethylaminomethylene}carbamate ethyl N-{1-[3-(3-chloro-4-nitrophenyl)-1-methylureido]-1-dimethylaminomethylene}carbamate ethyl N-{1-[3-(p-propylphenyl)-1-methylureido]-1-dimethylaminomethylene}carbamate methyl N-[1-(3-cyclohexyl-1-methylureido)-1-dimethylaminomethylene]thiolcarbamate methyl N-[1-(3-cycloheptyl-1-methylureido)-1-dimethylaminomethylene]thiolcarbamate methyl N-[1-(3-cyclopentyl-1-methylureido)-1-dimethylaminomethylene]thiolcarbamate methyl N-{1-[3-(2-methylcyclohexyl)-1-methylureido]-1-dimethylaminomethylene}thiolcarbamate methyl N-[1-(3-phenyl-1-methylureido)-1-dimethylaminomethylene]thiolcarbamate methyl N-{1-[3-(3,4-dichlorophenyl)-1-methylureido]-1-dimethylaminomethylene}thiolcarbamate methyl N-{1-[3-(2,4,5-trichlorophenyl)-1-methylureido]-1-dimethylaminomethylene}thiolcarbamate methyl N-[1-(3-norbornyl-1-methylureido)-1-dimethylaminomethylene]thiolcarbamate methyl N-[1-(3-norbornenyl-1-methylureido)-1-dimethylaminomethylene]thiolcarbamate methyl N-{1-[3-(cyclohexen-2-yl)-1-methylureido]-1-dimethyl-aminomethylene}thiolcarbamate ethyl N-[1-(3-cyclohexyl-1-methylureido)-1-dimethylaminomethylene]thiolcarbamate isopropyl N-[1-(3-cyclohexyl-1-methylureido)-1-dimethylaminomethylene]thiolcarbamate octyl N-[1-(3-cyclohexyl-1-methylureido)-1dimethylaminomethylene]thiolcarbamate methyl N-[1-(3-cyclohexyl-1-methylureido)-1-(N-methyl-N-ethylaminomethylene)]carbamate methyl N-[1-(3-cyclohexyl-1-methylureido)-1-(N-methyl-N-butylaminomethylene)]carbamate methyl N-[1-(3-cyclohexyl-1-methylureido)-1-(N-methyl-N-allylaminomethylene)]carbamate methyl N-[1-(3-cyclohexyl-1-methylureido)-1-(N-methyl-N-propargylaminomethylene)]carbamate methyl N-{1-[3-(p-methylthiophenyl)-1-methylureido]-1-dimethylaminomethylene}carbamate methyl N-{1-[3-(p-methoxyphenyl)-1-methylureido]-1-dimethylaminomethylene}carbamate methyl N-{1-[3-(2,3,5,6-tetramethylcyclohexyl)-1-methylureido]-1-dimethylaminomethylene}carbamate The compounds of Formulas (1) and (2) can be used wherever general weed control is desired, for example, in industrial areas, railroad rights-of-way, and around highway structures.

The precise amount of active material to be used in any given situation will vary according to the plant species and soil involved, the formulation used, the mode of application, prevailing weather conditions, foliage density, length of residual activity desired, and like factors. It is, therefore, not possible to recommend a rate of application suitable for all situations. Broadly speaking, the compounds of the invention are used at levels of about 1 to about 25 kilograms per hectare.

The compounds of the present invention may be combined in any other herbicide and are particularly useful in combination with 3-sec-butyl-5-bromo-6-methyluracil (bromacil), 3-(3,4-dichlorophenyl)-1,1-dimethylurea (diuron), 1,1'-dimethyl-4,4'-bipyridinium salt (paraquat), 1,1-dimethyl-3-(3-N-tert-butylcarbamoyloxyphenyl)urea, 4-amino-6-tert-butyl-3-methylthio-as-triazin-5(4H)-one, and s-triazines such as 2-chloro-4-ethylamino-6-isopropylamino-s-triazine, for controlling a broad spectrum of weeds.

Many of the compounds of this invention possess unusually high water solubility, up to several percent. This offers an advantage in, for instance, control of brush and other deep-rooted, perennial weeds. An example of a highly water-soluble compound of this invention is methyl N-(N-cyclohexylcarbamoyl-N',N'-dimethylamidino)-N-methylcarbamate; this compound exhibits a solubility in water of about 22.7% at 25° C.

The herbicidal activity of the compounds of this invention was discovered in a greenhouse test. In this test seeds of crabgrass (Digitaria spp.), barnyardgrass (Echinochloa crusgalli), sorghum (Sorghum vulgare), wild oats (Avena fatua), Cassia tora, morningglory (Ipomoea spp.), radish (Raphanus spp.), marigold (Tagetes spp.), dock (Rumex crispus), and nutsedge (Cyperus rotundus) tubers were planted in a growth medium and treated preemergence at two rates (11 and 2.2 kg. per hectare) with the chemical dissolved in a nonphytotoxic solvent. Johnsongrass (Sorghum halepense) having four leaves, crabgrass and barnyardgrass with three leaves and nutsedge from tubers with two leaves were treated postemergence at 11 kg per hectare, and bush beans with the third trifoliate leaf expanding and sorghum with four leaves were treated postemergence at 2.2 kg per hectare. Treated plants and controls were maintained in the greenhouse for 16 days, then all species were compared to controls and visually rated for responses to treatment. A quantitative rating was made on a scale of 0 to 10. A qualitative rating (type of injury) was also made.

The results obtained for methyl N-(N-cyclohexylcarbamoyl-N',N'-dimethylamidino)-N-methylcarbamate (I) and methyl N-[1-(3-cyclohexyl-1-methylureido)-1-dimethylaminomethylene]carbamate (II) are shown in Table III below, wherein 0 indicates no effect and 10 means that all plants are affected, i.e., complete kill. C indicates chlorosisnecrosis and G growth retardation.

|  | | Percent by Weight | | |
| --- | --- | --- | --- | --- |
|  | | Active Ingredient | Carrier | Surfactant |
| Wettable & Water-Soluble Powders | | 20–95 | 0–80 | 0–10 |
| Oil Suspensions, Emulsions, Solutions (including Emulsifiable Concentrates) | | 5–50 | 40–95 | 0–15 |
| Dusts | | 1–25 | 70–99 | 0–5 |
| Granules and Pellets | | 1–95 | 5–99 | 0–15 |
| High Strength Compositions | | 90–99 | 0–10 | 0–2 |

Lower or higher levels of active ingredient can, of course, be present depending on the intended use and the physical properties of the compound. Higher ratios of surfactant to active ingredient are sometimes desirable.

Typical solid carriers are described in Watkins et al., "Handbook of Insecticide Dust Diluents and Carriers", 2nd. Edn., Dorland Books, Caldwell, N.J., 1955. Less common carriers include sugars and inorganic salts. The more absorptive carriers are preferred for wettable powders and the denser ones for dusts. Typical liquid carriers are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Pbl. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the intended use.

The methods of making such compositions are well

TABLE III

| Compound | Kg. Per Hectare | POSTEMERGENCE | | | | PREEMERGENCE | | | | | | | | | | |
| --- | --- | --- | --- | --- | --- | --- | --- | --- | --- | --- | --- | --- | --- | --- | --- | --- |
|  |  | Nutsedge | Johnsongrass | Crabgrass | Barnyardgrass | Crabgrass | Barnyardgrass | Sorghum | Wild Oats | Nutsedge | Cassia | Morningglory | Mustard | Radish | Marigold | Dock |
| I | 11 | 9C | 10C | 10C | 10C | 10C | 10C | 10C | 10C | 4C | 10C | 10C | 10C | 10C | 10C | 10C |
|  | 2.2 |  |  |  |  | 10C | 10C | 10C | 10C | 3C | 10C | 10C | 10C | 10C | 10C | 10C |
| II | 2.2 | 0 | 8C | 8C | 7C | 9C | 10C | 9C | 10C | 0 | 10C | 10C | 10C | 10C | 10C | 10C |
|  | 0.4 |  |  |  |  | 9C | 10C | 4G | 6C | 0 | 10C | 10C | 10C | 10C | 10C | 10C |

Useful formulations of the compounds of Formulas (1) and (2) can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of at least one compound of Formulas (1) and (2) and either about 0.1% to 15% of a surfactant or about 1% to 99% of a solid or liquid carrier or both. More specifically, the formulations will contain these ingredients in the following approximate proportions:

known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques; see J. E. Browning, "Agglomeration", Chemical Engineering, Dec. 4, 1967, pp. 147ff. and "Perry's Chemical Engineer's Handbook", 4th. Edn., McGraw-Hill, N.Y., 1963, pp. 8–59ff.

For further information regarding the art of formulation, see for example:

H. M. Loux, U.S. Pat. No. 3,235,361.
R. W. Luckenbaugh, U.S. Pat. No. 3,309,192,
H. Gysin and E. Knusli, U.S. Pat. No. 2,891,855.
G. C. Klingman, "Weed Control as a Science", John Wiley & Sons, Inc., New York, 1961, pp. 81–96.

J. D. Fryer and S. A. Evans, "Weed Control Handbook", 5th Edn. Blackwell Scientific Publications, Oxford, 1968, pp. 101-103.

Typical formulations of compounds of the present invention are shown below:

| A. Wettable Powder | |
|---|---|
| Methyl N-(N-cyclohexylcarbamoyl-N',N'-dimethylamidino)-N-methylcarbamate | 40% |
| Dioctyl sodium sulfosuccinate | 1.5% |
| Sodium ligninsulfonate | 3% |
| Low viscosity methyl cellulose | 1.5% |
| Attapulgite | 54% |

The ingredients are thoroughly blended, passed through an air mill, to produce an average particle size under 15 microns, reblended, and sifted through a U.S.S. No. 50 sieve (0.3 mm opening) before packaging.

| B. Wettable Powder | |
|---|---|
| Methyl N-[1-(3-cyclohexyl-1-methylureido)-1-dimethylaminomethylene]carbamate | 70% |
| Sodium alkylnaphthalenesulfonate | 2% |
| Sodium N-methyl-N-oleoyltaurate | 2% |
| Diatomaceous earth | 26% |

The ingredients are blended and ground in a hammer mill so that only a few percent of the active exceeds 250 microns (U.S.S. #60 sieve) in size. After milling, the powder is reblended and sifted through a U.S.S. No. 50 sieve (0.3 mm opening) before packaging.

| C. Water Soluble Powder | |
|---|---|
| Methyl N-(N-cyclohexylcarbamoyl-N',N'-dimethylamidino)-N-methylcarbamate | 91.0% |
| Sodium alkylnaphthalenesulfonate | 0.5% |
| Magnesium sulfate heptahydrate | 7.8% |
| Synthetic fine silica | 0.7% |

The ingredients are blended and passed through a U.S.S. #40 sieve so that the particles do not exceed 420 microns in size. When added to water with stirring, the coarse powder initially disperses and then the active ingredient dissolves so that no further stirring is needed during application.

| D. Oil Suspension | |
|---|---|
| Methyl N-[N-(3-methylphenylcarbamoyl)-N',N'-dimethylamidino]-N-methylcarbamate | 25% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

| E. Extruded Pellet | |
|---|---|
| Methyl N-(N-phenylthiocarbamoyl-N',N'-dimethylamidino)-N-methylcarbamate | 25% |
| Anhydrous sodium sulfate | 10% |
| Crude calcium ligninsulfonate | 5% |
| Sodium alkylnaphthalenesulfonate | 1% |
| Calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

In the following composition claims, the expression "consisting essentially of" means that, in addition to the components recited in those claims, other components also may be present, provided they do not adversely affect the operability of the compositions for their intended use.

I claim:

1. A compound having one of the following formulas $$R_1NH-\overset{X}{\underset{\|}{C}}-N=C-\underset{R_2}{\overset{R_3\diagdown\phantom{0}\diagup R_4}{\underset{|}{N}}}-\overset{O}{\underset{\|}{C}}-R_5 \quad (1)$$

and $$R_1NH-\overset{X}{\underset{\|}{C}}-\underset{R_2}{\overset{|}{N}}-C=N-\overset{O}{\underset{\|}{C}}-R_5 \quad (2)$$

with $R_3$ and $R_4$ on the middle N.

wherein
$R_1$ is selected from a $C_2$-$C_8$ alkyl substituted with 0-1 methoxy, ethoxy, methylthio, or ethylthio group; a $C_3$-$C_6$ alkenyl; a $C_3$-$C_6$ alkynyl; a $C_4$-$C_8$ cycloalkyl substituted with 0-1 $C_2$-$C_4$ alkyl, 0-2 methyl groups, 0-2 chlorine or bromine atoms, or 0-1 methoxy or ethoxy group; a $C_5$-$C_8$ cycloalkenyl; a $C_4$-$C_8$ cycloalkylmethyl or cycloalkenylmethyl; a $C_7$-$C_{10}$ bicycloalkyl or bicycloalkenyl; a $C_8$-$C_{11}$ bicycloalkylmethyl or bicycloalkenylmethyl; trimethylcyclohexyl; tetramethylcyclohexyl; and a phenyl ring with substituents Q, Z, Y, H as shown.

wherein
Q is hydrogen, fluorine, chlorine, bromine, a $C_1$-$C_4$ alkyl, a $C_1$-$C_2$ alkoxy or alkylthio group, nitro or trifluoromethyl group;
Y is hydrogen, chlorine, or methyl; and
Z is hydrogen or chlorine;
$R_2$ is a $C_1$-$C_3$ alkyl;
$R_3$ is hydrogen, methyl, or ethyl;
$R_4$ is a $C_1$-$C_4$ alkyl, a $C_3$-$C_4$ alkenyl, a $C_3$-$C_4$ alkynyl, or methoxyl;
$R_5$ is —$SR_6$, wherein $R_6$ is a $C_1$-$C_8$ alkyl substituted with 0-3 chlorine atoms or 0-1 methoxyl; and
X is oxygen or sulfur.

* * * * *